(12) United States Patent
Brandts

(10) Patent No.: US 10,814,310 B2
(45) Date of Patent: Oct. 27, 2020

(54) TITANIUM STANNATE SILICATE, METHOD OF PREPARATION AND USE THEREOF

(71) Applicant: BASF Corporation, Florham Park, NJ (US)

(72) Inventor: Jim Aloysius Maria Brandts, De Meern (NL)

(73) Assignee: BASF CORPORATION, Florham Park, NJ (US)

( * ) Notice: Subject to any disclaimer, the term of this patent is extended or adjusted under 35 U.S.C. 154(b) by 1415 days.

(21) Appl. No.: 14/782,665

(22) PCT Filed: Apr. 10, 2014

(86) PCT No.: PCT/IB2014/060621
§ 371 (c)(1),
(2) Date: Oct. 6, 2015

(87) PCT Pub. No.: WO2014/167524
PCT Pub. Date: Oct. 16, 2014

(65) Prior Publication Data
US 2016/0067677 A1   Mar. 10, 2016

(30) Foreign Application Priority Data

Apr. 11, 2013 (EP) .................................. 13163288

(51) Int. Cl.
*B01J 23/14* (2006.01)
*B01J 37/03* (2006.01)
(Continued)

(52) U.S. Cl.
CPC .............. *B01J 23/14* (2013.01); *B01J 20/10* (2013.01); *B01J 20/103* (2013.01);
(Continued)

(58) Field of Classification Search
None
See application file for complete search history.

(56) References Cited

U.S. PATENT DOCUMENTS 5,053,139 A   10/1991  Dodwell et al.
5,192,519 A    3/1993  Corcoran et al.
(Continued)

FOREIGN PATENT DOCUMENTS

EP    0 027 736    4/1981
GB      212065     3/1924
WO   2010101991    9/2010

OTHER PUBLICATIONS

Ma, et al., Characterization and reactivity of stannum modified titanium silicalite TS-1 catalysts for transesterification of dimethyl oxalate and phenol, Journal of Molecular Catalysis A: Chemical, Aug. 2, 2005, pp. 1-8, vol. 237, No. 1-2, Elsevier, Amsterdam, NL.
(Continued)

*Primary Examiner* — Clinton A Brooks
(74) *Attorney, Agent, or Firm* — Lowenstein Sandler LLP

(57) ABSTRACT

The present invention relates to an amorphous titanium stannate silicate with the general formula: $M^{v+}{}_w Ti_x Si_y Sn_z O_{2x+2y+2z+0.5vw}$, wherein M is proton, ammonium, a metal or a mixture of metals, wherein v is the valence of M being a positive integer, and wherein x, y, z and w are molar ratios: x is 1, y is from 0.01 to 99, z is from 0.01 to 99, and w is from 0.01 to 50. The described titanium stannate silicates are particularly useful in catalysis and adsorption.

17 Claims, 1 Drawing Sheet

(51) Int. Cl.
  B01J 35/10    (2006.01)
  C01B 33/20    (2006.01)
  B01J 37/02    (2006.01)
  G21F 9/12     (2006.01)
  B01J 39/14    (2006.01)
  C02F 1/28     (2006.01)
  B01J 21/08    (2006.01)
  B01J 20/10    (2006.01)
  B01J 21/06    (2006.01)
  B01J 20/28    (2006.01)
  B01J 20/30    (2006.01)
  B01J 35/02    (2006.01)
  B01J 37/08    (2006.01)
  B01J 37/30    (2006.01)
  C07C 67/08    (2006.01)
  C02F 103/06   (2006.01)
  C02F 101/20   (2006.01)
  C02F 101/00   (2006.01)
  C02F 101/32   (2006.01)

(52) U.S. Cl.
  CPC ... *B01J 20/28071* (2013.01); *B01J 20/28083* (2013.01); *B01J 20/3078* (2013.01); *B01J 20/3085* (2013.01); *B01J 21/063* (2013.01); *B01J 21/08* (2013.01); *B01J 35/026* (2013.01); *B01J 35/1019* (2013.01); *B01J 35/1038* (2013.01); *B01J 35/1042* (2013.01); *B01J 35/1061* (2013.01); *B01J 37/0201* (2013.01); *B01J 37/031* (2013.01); *B01J 37/08* (2013.01); *B01J 37/30* (2013.01); *B01J 39/14* (2013.01); *C01B 33/20* (2013.01); *C02F 1/281* (2013.01); *C02F 1/288* (2013.01); *C07C 67/08* (2013.01); *G21F 9/12* (2013.01); *C01P 2006/14* (2013.01); *C01P 2006/16* (2013.01); *C02F 2101/006* (2013.01); *C02F 2101/20* (2013.01); *C02F 2101/327* (2013.01); *C02F 2103/06* (2013.01)

(56) References Cited

U.S. PATENT DOCUMENTS 5,780,654 A    7/1998  Nemeth et al.
6,074,624 A    6/2000  Nemeth et al.

OTHER PUBLICATIONS

International Search Report and Written Opinion for PCT/IB2014/060621, dated May 27, 2014, 13 pgs.

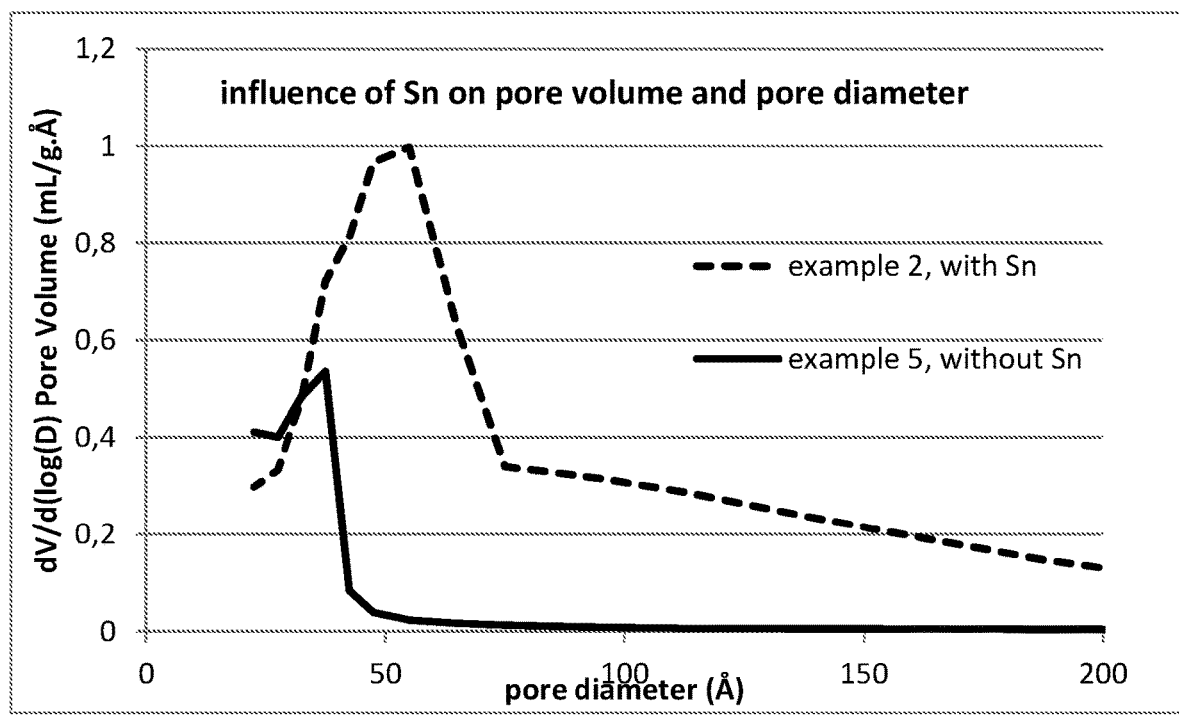

TITANIUM STANNATE SILICATE, METHOD OF PREPARATION AND USE THEREOF

The invention relates to the field of silicates useful as catalysts and adsorbents, particularly silicates containing transition metals such as titanium.

Mesoporous silicate materials have numerous applications in broad areas as catalysts and sorption media due to their large surface area and pores of a predetermined diameter. This makes them particularly suitable for use as purifying adsorbents, catalysts, catalyst carriers, filter medium, fillers.

In particular, U.S. Pat. No. 5,508,457 describes Group IVB silicates, particularly of titanium and zirconium, which can be crystalline or amorphous. Described catalysts are inter alia crystalline titanium silicate, crystalline titanium aluminium silicate, amorphous titanium silicate and the corresponding zirconium compounds. The silicates are useful in (trans)esterification reactions, and especially in a fixed bed process.

U.S. Pat. No. 5,053,139 describes amorphous titanium silicates and tin silicates that can be used to remove lead from drinking water in the presence of competing ions normally found in said drinking water.

GB 212,065 describes a method of preparing a plural oxide gel by mixing an acid with a solution of a soluble salt, such of a sodium salt of the acid of tin oxide, aluminium oxide, tungsten oxide and/or titanium oxide to produce a hydrogel. The final product of this method is described as being a highly porous substance having ultramicroscopic pores. Also described is the preparation of a stannate tungstate gel by mixing solutions of sodium stannate, sodium tungstate and an acid to produce a hydrogel. However, no example is described in which a soluble titanate salt is used and the only titanate salt suggested for use is sodium titanate, which is practically insoluble in water.

While various silicates already exist, there is always a need for new compounds for catalysis and sorption applications with improved physical properties, such as pore size, and improved catalyst properties such as selectivity and activity.

In order to address at least one of the foregoing desires, the present invention provides an amorphous titanium stannate silicate with the general formula:

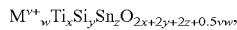

$$M^{v+}{}_w Ti_x Si_y Sn_z O_{2x+2y+2z+0.5vw},$$

wherein M is at least one of proton, ammonium, a metal or a mixture of metals, v is the valence of M being a positive integer and wherein x, y, z and w are molar ratios:

x is 1,
y is from 0.01 to 99,
z is from 0.01 to 99, and
w is from 0.01 to 50.

In another aspect, the present invention provides a method for the preparation of the titanium stannate silicate according to the invention comprising a precipitation reaction in an aqueous medium between a soluble silicate source, a soluble stannate source and a soluble titanium source, whereby the titanium stannate silicate is precipitated and isolated.

In a further aspect, the present invention provides the use of the titanium stannate silicate according to the invention, as a catalyst or catalyst support in a chemical reaction, or as an adsorbent.

The titanium stannate silicate according to the invention is different from existing titanium and tin silicates in that all the three elements make up the oxygen network. On the structural level, the compound of the invention represents a three-dimensional oxide network composed of interconnected silicate, titanate and stannate polyhedra. Therefore, all the three atoms—Si, Ti and Sn—make up a part of the network of oxygen —O— bonds. In an alternative view, it can be said that the Sn atoms replace the Ti (or Si) atoms of the network of Ti and Si bonded through oxygen —O— bonds. It can also be said that the compound according to the invention is a mixed oxide of titanium, tin and silicon. The difference with Ti/Sn/Si compounds obtained from titanium silicates by ion exchange with Sn cations, is in that tin is present in the compound according to the invention not as a cation but is covalently bound to oxygen atoms, that is in the form of a stannate. Also, tin is present in the compound according to the invention as Sn(IV), while by ion exchange Sn(II) is usually introduced. Also the term "stannate" particularly means that tin is present as Sn(IV) in the structure.

The described structure of the titanium stannate silicate is clearly different from the structures obtained by impregnation with tin salts, wherein Sn is present as $Sn^{2+}$ cation. Examples of the cation exchange in titanium silicates (amorphous) and titanium silicates (crystalline e.g. TS-1, ETS-4) with cationic tin compounds like $SnCl_2$, are described in [Journal of Molecular Catalysis A: Chemical (2005), 237 (1-2), 1-8] and [Chemical Communications (2003), (13), 1500-1501]. However, loading of Sn is limited to the amount of exchangeable cations as tin cation only weakly binds to the surface of the Ti/Si-oxide structure having Si—O or Ti—O groups. In the present invention the amount of Sn incorporated in the structure can be varied and can be very high, such as at least 30 wt. %, or at least 50 wt. %, or even as high as at least 70 wt. %. Theoretically, the maximum amount of Sn that can be present in the titanium stannate silicate of the invention is 78 wt. % calculated for an almost pure $SnO_2$ with traces of $SiO_2/TiO_2$. During the preparation of the compound of the invention, the Sn is not added as a cation but as an anion, $SnO_3^{2-}$ such as $Na_2SnO_3$. The introduction of Sn in the oxide network according to the present invention surprisingly leads to improved physical and catalytic properties, as described in more details hereinbelow.

The structure and the environment of the Sn atom can be determined by different techniques, for example XPS, UV-Vis or solid state NMR. In addition, Sn introduced by ion exchange always influences the weight ratio of M to Sn. This means that molar ratios w and z as used in the general formula are interrelated in case of ion exchange introduction, while in the present invention these values can be chosen independently from each other. For example, during ion exchange a single ion of Na is exchanged for a single ion of Sn. In the present invention, however, the Sn is built-in as stannate in the oxide structure and therefore does not influence the amount of Na or H that can be bound at the surface of the titanium stannate silicate.

The titanium stannate silicate according to the invention is present in the amorphous form. Under amorphous form an X-ray amorphous is meant, that is, a solid form whose X-ray powder diffraction pattern contains no crystalline diffraction peaks. As found by the inventors, the titanium stannate silicate in the amorphous form allows control over a wide range of molar ratios between Ti:Si:Sn, which may in turn result in better tuning of material properties and therefore catalytic and adsorption properties. In addition, the amorphous form has particularly good catalytic properties in esterification and transesterification reactions.

The titanium stannate silicate according to the invention has the following general formula: $M^{v+}{}_w Ti_x Si_y Sn_z O_{2x+2y+2z+0.5vw}$. In this formula, M represents at least one of H (proton), ammonium, a metal or a mixture of metals. The metal can be an alkali metal, an alkali earth metal, a transition metal or another metal, such as a metal with valence 1, 2 or 3. In a preferred embodiment, M is at least one of proton, ammonium, Na, Li, K, Cs, Ca, Mg, Sr, Ba, Fe(II), Fe(M), Sn(II), Ce, La, Nb, Ni, V, W, Mo, Al, Zn, Cu, Mn. In one preferred embodiment, the M is a proton, ammonium, an alkali metal or an alkali earth metal. In another preferred embodiments, M represents Li, Cs, Mg, Ca, Sr, Ba, La, Nb, Fe, Ni, V, W, Mo, Al, Ce, Sn, Zn, Cu, Mn ions or a combination of these.

Element M has a valence v, which is a positive integer. Preferably, the valence v of M is 1, 2, 3, 4, 5 or 6. In one preferred embodiment, v is 1, 2 or 3. In another preferred embodiment, v can be 5 or 6. The values x, y, z and w are molar ratios and are in particular as follows: x is 1, y is from 0.01 to 99, z is from 0.01 to 99, and w is from 0.01 to 50. Preferably, y is in the range 0.1-10, more preferably, 0.2-5. Preferably, z is in the range 0.03-5, more preferably 0.05-1. Preferably, w is in the range 0.01-50, more preferably, 0.1-10. As mentioned earlier, the values of w and z can be adjusted in an independent from each other way.

Surprisingly, by incorporating $SnO_2$ in the titanium silicate structure (or by incorporating $TiO_2$ into the tin silicate structure), the physical and catalytic properties of the resulting materials can be modified.

Even more surprisingly, the pore volume of the material according to the invention is higher than what is typically found for amorphous titanium silicate materials: usually far below 0.3 mL/g. For example, U.S. Pat. No. 5,053,139 reports a pore volume between 0.03 and 0.25 mL/g. The titanium stannate silicate according to the invention has a pore volume of at least 0.3 mL/g. Along with the increased pore volume of the titanium stannate silicate materials, a larger average pore diameter is found, typically having mesopores and/or macropores, as classified by IUPAC 1994, which have pore diameters of 2-50 nm and >50 nm, respectively. Typical average pore diameter values of the titanium stannate silicate materials are at least 40 Å, more preferably at least 60 Å. Traditional amorphous titanium silicate has an average pore diameter between 30 and 35 Å. The BET surface of the titanium stannate silicate of the invention is from 100 to 600, preferably from 200 to 500 m²/g.

The BET surface area, as used herein, is the value that is measured by liquid nitrogen adsorption and in particular by determining the amount of nitrogen adsorbed at 77 K and $P/P_0$ of approximately 0.3 and assuming a nitrogen cross sectional area of 16.2 Å², after degassing the sample at 180° C. on a Micromeritics ASAP 2420. The total pore volume, as used herein, is the value measured by determining the volume of liquid nitrogen adsorbed at $P/P_0$ of approximately 1 using a Micromeritics ASAP 2420. The average pore diameter, as used herein, is the value determined by dividing the total pore volume by the BET surface area, and assuming that the pores are cylindrical. The BJH method can be used to calculate the pore size distributions from experimental isotherms using the Kelvin model of pore filling.

The titanium stannate silicate of the invention is preferably in the form of powder, tablets, granules or extrudate, more preferably in the form of tablets or extrudate.

Surprisingly, the present inventors have found that the new tin-containing materials according to the invention have improved catalytic properties compared to the amorphous titanium silicate. For example, the material of the invention used as a catalyst is more active towards the conversion of triglycerides with methanol to fatty acid methyl esters, compared to amorphous titanium silicates. Also the material of the invention is more active in the esterification of free fatty acids with methanol to form fatty acid methyl esters.

The present invention provides, in another aspect, a method for the preparation of the titanium stannate silicate of the invention. This method comprises a precipitation reaction in an aqueous medium between a soluble silicate, a soluble stannate and a soluble titanium source, whereby the titanium stannate silicate is precipitated and isolated. As a silicate source, preferably soluble silicate salts are used, such as $Na_2SiO_3$. As a stannate source, preferably soluble stannate salts are used, such as $Na_2SnO_3$. Suitable titanium sources are for example titanium salts and titanium oxy salts, such as $TiOCl_2$. Particularly suitable are titanium (IV) compounds such as $TiCl_4$, titanium(IV) bromide, titanium (IV) fluoride, titanium(IV) iodide, titanium(IV) alkoxides, TiO-alkoxides, however titanium (III) can also be used.

The precipitate is obtained in the form of a substance which is isolated from the solution, preferably by filtration. To obtain the TiSiSn materials that are useful for catalytic and sorption applications water from the substance should be removed to obtain a solid product. Drying can be done at elevated temperatures, such as 80-120° C., but can also be done at the room temperature. The drying can be performed in the air, or in a nitrogen flow. Drying can also be preceded by a washing step to remove the salt formed during the precipitation.

Alternatively to the drying step, or after the drying step, the solid material can be calcined, for example at a temperature of above 200° C., preferably above 300° C., more preferably above 400° C. Calcination at higher temperatures may make the materials more active as a catalyst. The other reason when calcination at higher temperatures is preferred is when tablets using a lubricant are prepared. In this case the lubricant, e.g. hydrogenated fats or graphite, needs to be burned off without effecting the amorphous character of the TiSiSn-structure.

The titanium stannate silicate of the invention remains amorphous, even after calcination at 450° C. The present inventors observed that without the presence of silicon oxide, the formed compound is titanium stannate which is crystalline already after drying at 110° C. and it remains crystalline also after calcination at 450° C. Such material with no Si built in (100% TiSn, see Example 4) shows considerably less activity in the esterification and transesterification reactions.

The method according to the invention can further comprise at least one step of ion exchange. For example, at least a part of the cations present in the precipitate after the precipitation reaction can be exchanged by protons ($H^+$). The protonated titanium stannate silicate may be less prone to degrade and dissolve in the feed or product stream. Replacing part of the cations (such as $Na^+$ or $K^+$) with $H^+$ may also have the advantage that the esterification activity of the catalyst increases. Typically the amount of Na or K ions is around 5-10 wt. % in fresh catalysts (i.e. prior to contacting them with feedstock, in particular with (fatty) acids). This Na or K content can be lowered by exchanging with H+ to less than 3 wt. %. More preferably, the sodium or potassium content is lowered by exchanging with $H^+$ to less than 1 wt. %, even more preferably to around 0.1 to 0.2 wt. %. Instead of $H^+$ other cations may be used to exchange the Na or K ions, such $NH_4^+$, $Cs^+$ or $Ca^{2+}$. The step of ion exchange can be carried out after the precipitation and before the drying step, if present, or after the drying step, if present, or even after calcination.

It was also found that the thermal stability of the materials can be influenced by ion exchange. Particularly, it was found that when sodium is exchanged for a proton, the calcination temperature at which crystallinity is detected with XRD measurements, is much higher. It is believed that the height of the calcination temperature has an influence on the BET-SA, pore volume and average pore diameter of the materials. Therefore, a higher temperature at which crystallinity is detected means increased thermal stability of the material.

In a preferred embodiment, the ion exchange is performed with a cation selected from proton, ammonium, Na, K, Li, Cs, Mg, Ca, Sr, Ba, La, Nb, Fe, Ni, V, W, Mo, Al, Ce, Sn, Zn, Cu, Mn ions, and combinations thereof. The cations may be introduced in the structure in order to improve activity and/or selectivity of the resulting compound in catalytic reactions.

The material according to the present invention can be used in a variety of applications. Especially preferred is the use of this material in catalytic reactions such as esterifications, Michael additions, transesterifications, (ep)oxidations, hydroxylations. The titanium stannate silicate of the present invention is preferably used as catalysts or catalyst supports, as such or after modification by ion exchange. The material of the invention can also be used as an ion exchanger. Further uses of the titanium stannate silicate of the invention are adsorbance of small inorganic and organic molecules e.g. $CO_2$ or aromatic compounds.

Another preferred use of the titanium stannate silicate of the invention is their use for the adsorption and removal of radionuclides, preferably Sr (particularly $^{90}$Sr) or actinides, from aqueous solutions. The material of the invention can therefore be used as a sorbent for the treatment of metal-contaminated waste streams and ground waters.

A further use of the material of the invention is for the selective adsorption and desorption of metals under physiological conditions, preferably Pt(II), Pt(IV), Pd, Gd, Hg, Cd, Au or Ho.

The material of the invention can be used in the form of a powder, tablet, granules, extrusions etc. It can be used as bulk material or on a support.

The invention will now be illustrated in the following, non-limiting examples. Where percentages or parts are mentioned, the percentages or parts by weight are meant unless stated otherwise.

EXAMPLE 1

Preparation of Na:Ti:Si:Sn with Molar Ratios of 0.29:1:1.02:0.06

In a vessel containing 95 g of demi-water there were dissolved 27.6 mL of a 30% NaOH solution, 10 mL of a 27% $Na_2SiO_3$ solution and 6.8 mL of a 13.5 wt % solution of $Na_2SnO_3$. The solution in this vessel is called solution A. In another vessel containing 112 g of demi-water, 16 mL of a 35% $TiOCl_2$ solution was added. The solution in this vessel is called solution B. Then, solution A is added to solution B in 5 minutes with vigorous stirring. After the addition is complete, the mixture is allowed to continue mixing for an additional 10 minutes. The pH of the solution should fall between 7.5 and 7.9; if necessary, the pH is adjusted with dilute HCl or dilute NaOH. The sample is then allowed to age for more than 4 hours (up to 4 days). The slurry was filtered and the remaining substance was dried in the oven overnight at 110° C. The resulting white solids were granulated, sieved through a 425 μm sieve, reslurried in water and stirred for 1 h. Subsequently, the slurry was filtered, washed with demi-water until the conductivity of the wash water was below 200 μS/cm. The resulting white material was dried in the oven overnight at 110° C. Approximately 12.5 g of white solids were produced by method.

The material is amorphous (XRD) and had a Na:Ti:Si:Sn ratio of 0.29:1:1.02:0.06 and a pore volume of 0.47 mL/g, BET-SA=430 m²/g, average pore diameter=52 Å.

EXAMPLE 2

Preparation of Na:Ti:Si:Sn with Molar Ratios of 0.23:1:0.34:0.18

A similar procedure as described in Example 1 was used but with different amounts of starting materials. Solution A contained 95 g of demi-water, 26.7 mL of a 30% NaOH solution, 3.4 mL of a 27% $Na_2SiO_3$ solution and 20 mL of a 13.5 wt. % solution of $Na_2SnO_3$. Solution B was similar to example 1. Approximately 10.8 g of white solids were produced.

The material is amorphous (XRD) and had a Na:Ti:Si:Sn molar ratio of 0.23:1:0.34:0.18 and a pore volume of 0.48 mL/g. BET-SA=431 m2/g, average pore diameter=51 Å.

EXAMPLE 3

Preparation of a H+ Exchanged Material

A similar procedure as described in example 1 was used but with different amounts of starting materials. Solution A contained 380 g of demi-water, 105 mL of a 30% NaOH solution, 13.7 mL of a 27% $Na_2SiO_3$ solution and 80.8 mL of a 13.5 wt. % solution of $Na_2SnO_3$. Solution B was prepared by adding 64.5 mL of a 35% $TiOCl_2$ solution to 450 g of demi-water. Then, solution A is added to solution B in 10 minutes with vigorous stirring. After the addition is complete, the mixture is allowed to continue mixing for an additional 10 minutes. The pH of the solution should fall between 7.5 and 7.9; if necessary, the pH is adjusted with dilute HCl or dilute NaOH. To the mixture 40 g of NaCl was added (optional). The sample is then allowed to age for more than 4 hours. The slurry was filtered and the remaining substance was dried in the oven overnight at 110° C. After drying, the white solids were granulated, sieved through a 425 μm sieve, reslurried in water and stirred for 1 h at a pH 2.0 (pH adjustment with 10% HCl). Subsequently, the slurry was filtered, washed with demi-water until the conductivity of the wash water was below 200 μS/cm. The resulting white material was dried in the oven overnight at 110° C. Approximately 40.7 g of white solids were produced by method.

The material is amorphous as confirmed by XRD, and had a Na:Ti:Si:Sn molar ratio of 0.01:1:0.34:0.16 and a pore volume of 0.50 mL/g. BET-SA=384 m²/g, average pore diameter=55 Å.

EXAMPLE 4

Preparation without Si

A similar procedure as described in example 1 was used but with different amounts of starting materials. Solution A contained 90 g of demi-water, 24.3 mL of a 30% NaOH solution and 25 mL of a 13.5 wt. % solution of $Na_2SnO_3$. Solution B was containing 100 g of demi-water and 15 mL of a 35% $TiOCl_2$ solution. Then, solution A is added to solution B in 5 minutes with vigorous stirring. After the addition is complete, the mixture is allowed to continue mixing for an additional 10 minutes. The pH of the solution should fall between 7.5 and 7.9; if this is not the case, the pH is adjusted with dilute HCl or dilute NaOH. To the mixture 10 g of NaCl was added (optional). The sample is then allowed to age for more than 4 hours (up to 4 days). The slurry was filtered and the remaining substance was dried in the oven overnight at 110° C. The resulting white solids were granulated, sieved through a 425 μm sieve, reslurried in water and stirred for 1 h at a pH 2.0 (pH adjustment with 10% HCl). Subsequently, the slurry was filtered, washed with demi-water until the conductivity of the wash water was below 200 μS/cm. The resulting white material was dried in the oven overnight at 110° C. Approximately 8.2 g of white solids were produced by method.

The material is crystalline as confirmed by XRD, and had a Na:Ti:Si:Sn molar ratio of 0.01:1:0:0.24 and a pore volume of 0.30 mL/g, BET-SA=256 m$^2$/g, average pore diameter=39 Å.

Calcination of Examples 1, 2, 3 and 4

The samples prepared by Example 1, 2, 3 and 4 were calcined in air at 450° C. for 2 hours. After calcination all samples remained amorphous, except the material from Example 4 that remained crystalline.

EXAMPLE 5

TiSi Traditional Synthesis

Titanium silicate powder was made in accordance with Example 9 of U.S. Pat. No. 5,053,139: Two litres of a 1.5 M titanium chloride solution (solution A) were made by adding 569.11 g TiCl$_4$ to enough deionized water to make 2 litres. Two litres of 1.5M sodium silicate solution (solution B) are made by dissolving 638.2 g of Na$_2$SiO$_3$.5H$_2$O in enough 3M NaOH to make 2 litres. Solution B is added to solution A at a rate of 16 cc/minute with extremely vigorous stirring. After addition is complete, the mixture is allowed to continue mixing for an additional 15 minutes. The pH of the solution should fall between 7.5 and 7.9; if this is not the case, the pH is adjusted with dilute HCl or dilute NaOH. The sample is then allowed to age 2-4 days. After aging, any water on top of the substance is decanted off. The sample is then filtered, washed with 1 litre deionized water per litre of substance, reslurried in 4-6 litres of deionized water, filtered, and finally rewashed in 2 litres of water per litre of substance.

For efficiency reasons, the sample was then dried at 105° C. for 24 hours (until LOI is below 10). At no time during the synthesis procedure is the substance allowed to contact any metal; polypropylene and glass labware are used throughout the preparation.

The solids produced from this method were granulated and sieved to particles below 250 micron and the resulting had a sodium:titanium:silicon molar ratio of 0.35:1:0.96 and a pore volume around 0.14 mL/g, BET-SA=364 m$^2$/g, average pore diameter=31 Å.

FIG. 1 shows the pore size distribution of the products obtained in Examples 2 and 5. It can be seen that the presence of Sn built in the structure (Example 2) results in a significantly larger pore volume in comparison with a compound without Sn (Example 5).

EXAMPLE 6

Cation Exchange by TiSi Modification with SnCl$_2$

In a glass beaker 50.0 g of titanium silicate prepared according to Example 5 was slurried in 450 mL demi-water. To this slurry was added 29.34 g SnCl$_2$.2H$_2$O as a solid. The colour of the mixture changes from white to yellow. The pH of the slurry changed from 8.80 to 1.60. The mixture was allowed to stir for an additional 2 hours at room temperature. After 2 hours the slurry was filtered and washed with demi-water until the conductivity of the filtrate was below 20 microSiemens/cm. The yellowish filtercake was dried in an oven overnight at 110° C. yielding 48.2 g of a yellow powder. The resulting material was amorphous by XRD.

The material had a Na:Ti:Si:Sn molar ratio of 0.01:1:1.27:0.19. The pore volume measured is 0.14 mL/g, the BET surface is 229 m$^2$/g, the average pore diameter is 32 Å.

EXAMPLE 7

Preparation of Tablets

The material of Example 3 was mixed with graphite and was tableted to a size of 1.5×1.5 mm. The resulting tablets were calcined @ 500° C. for 2 hours.

EXAMPLE 8

Use of TiSi in Simultaneous Esterification and Transesterification 10 mL of titanium silicate tablets were made from the material prepared according to Example 5 but in which the Na content was lowered by HCl treatment at pH 2.00. After filtration, washing and drying the material contains 0.8 wt. % Na. This material was tableted into 1.5*1.5 mm tablets. The tablets were loaded in a fixed bed reactor. The reactor was continuously fed with MeOH (1.73 mL/h) and rapeseed oil (3.47 mL/h) whereto 5 wt. % dodecanoic acid had been added. Reaction conditions were 180° C., 28 bars N$_2$ back pressure, LHSV rapeseed oil 0.347 h$^{-1}$ (3.47 mL/h), LHSV MeOH 0.173 h$^{-1}$ (1.73 mL/h).

Conversion of the triglyceride to fatty acid methyl esters was 46% and 99.1% of the dodecanoic acid was converted into the corresponding methyl ester.

EXAMPLE 9

Use of TiSiSn in Simultaneous Esterification and Transesterification 10 mL of titanium stannate silicate tablets prepared from material prepared according to Example 3. The tablets were loaded in a fixed bed reactor. The reactor was continuously fed with MeOH (1.73 mL/h) and rapeseed oil (3.47 mL/h) whereto 5 wt % dodecanoic acid had been added. Reaction conditions were 180° C., 28 bar N$_2$ back pressure, LHSV rapeseed oil 0.347 h$^{-1}$ (3.47 mL/h), LHSV MeOH 0.173 h$^{-1}$ (1.73 mL/h).

Conversion of the triglyceride to fatty acid methyl esters was 60% and 99.8% of the dodecanoic acid was converted into the corresponding methyl ester.

The invention claimed is:

1. Amorphous titanium stannate silicate with the general formula:

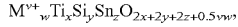

$$M^{v+}{}_w Ti_x Si_y Sn_z O_{2x+2y+2z+0.5vw},$$

wherein M is at least one of a proton, ammonium, a metal or a mixture of metals, v is the valence of M being a positive integer and wherein x, y, z and w are molar ratios:

x is 1, y is from 0.1 to 5, z is from 0.03 to 1, and w is from 0.01 to 10, and wherein said titanium stannate silicate has an average pore diameter of at least 40 Å, determined by liquid nitrogen adsorption.

2. The titanium stannate silicate according to claim 1, wherein M is at least one of proton, ammonium, Na, Li, K, Cs, Ca, Mg, Sr, Ba, Fe(II), Fe(III), Sn(II), Ce, La, Nb, Ni, V, W, Mo, Al, Zn, Cu, Mn.

3. The titanium stannate silicate according to claim 1, wherein w is in the range 0.1-10.

4. The titanium stannate silicate according to claim 1, wherein said titanium stannate silicate has a pore volume of at least 0.3 mL/g, determined by liquid nitrogen adsorption.

5. The titanium stannate silicate according to claim 1 having a form of powder, tablets, granules or extrudate.

6. A method for titanium stannate silicate preparation, the method comprising:

reacting a soluble silicate source, a soluble stannate source and a soluble titanium source in an aqueous medium to form titanium stannate silicate, precipitating the titanium stannate silicate, and isolating the titanium stannate silicate, the titanium stannate silicate having the general formula:

$$M^{v+}{}_w Ti_x Si_y Sn_z O_{2x+2y+2z+0.5vw},$$

wherein M is at least one of a proton, ammonium, a metal or a mixture of metals, v is the valence of M being a positive integer and wherein x, y, z and w are molar ratios:

x is 1, y is from 0.1 to 5, z is from 0.03 to 1, and w is from 0.01 to 10, and wherein said titanium stannate silicate has an average pore diameter of at least 40 Å, determined by liquid nitrogen adsorption.

7. The method according to claim 6, further comprising ion exchanging with a cation selected from proton, ammonium, Na, Li, K, Cs, Ca, Mg, Sr, Ba, Fe(II), Fe(III), Sn(II), Ce, La, Nb, Ni, V, W, Mo, Al, Zn, Cu, Mn ions, and combinations thereof.

8. The method according to claim 6, wherein the titanium stannate silicate is further calcined at a temperature of above 200° C.

9. A method comprising:

introducing into a chemical reaction an amorphous titania stannate silicate with the general formula:

$$M^{v+}{}_w Ti_x Si_y Sn_z O_{2x+2y+2z+0.5vw},$$

wherein M is at least one of a proton, ammonium, a metal or a mixture of metals, v is the valence of M being a positive integer and wherein x, y, z and w are molar ratios:

x is 1, y is from 0.1 to 5, z is from 0.03 to 1, and w is from 0.01 to 10, and wherein said titania stannate silicate has an average pore diameter of at least 40 Å, determined by liquid nitrogen adsorption.

10. The method according to claim 9, wherein the chemical reaction is a reaction of esterification, Michael addition, transesterification, oxidation, epoxidation, or hydroxylation.

11. A method for adsorption and desorption of metals from a metal-contaminated waste stream and ground water, the method comprising:

introducing an amorphous titania stannate silicate having the general formula:

$$M^{v+}{}_w Ti_x Si_y Sn_z O_{2x+2y+2z+0.5vw},$$

wherein M is at least one of a proton, ammonium, a metal or a mixture of metals, v is the valence of M being a positive integer and wherein x, y, z and w are molar ratios:

x is 1, y is from 0.1 to 5, z is from 0.03 to 1, and w is from 0.01 to 10; and contacting the amorphous titania stannate silicate with a metal contaminated stream, wherein said titania stannate silicate has an average pore diameter of at least 40 Å, determined by liquid nitrogen adsorption.

12. The method of claim 11 further comprising selectively adsorbing and desorbing metals in the metal contaminated stream.

13. The method according to claim 12, wherein the metals comprise Pt (II), Pt(IV), Pd, Gd, Hg, Cd, Au or Ho.

14. The method according to claim 11, wherein y is in the range of 0.2-5.

15. The method according to claim 11, wherein z is in the range of 0.05-1.

16. The method according to claim 11, further comprising adsorbing and removing radionuclides.

17. The method of claim 16, wherein the radionuclides comprise $^{90}$Sr or actinides.

* * * * *